(12) United States Patent
Kuo et al.

(10) Patent No.: US 6,214,803 B1
(45) Date of Patent: Apr. 10, 2001

(54) PHARMACOLOGICAL COMPOSITION FOR TREATING CANCER CELLS

(75) Inventors: Kou-Wha Kuo; Chun-Nan Lin, both of Kaohsiung (TW)

(73) Assignee: Committee on Chinese Medicine and Pharmacy Department of Health Executive Yuan, Taipei (TW)

( * ) Notice: Subject to any disclaimer, the term of this patent is extended or adjusted under 35 U.S.C. 154(b) by 0 days.

(21) Appl. No.: 09/435,521

(22) Filed: Nov. 8, 1999

(30) Foreign Application Priority Data

Aug. 25, 1999 (TW) .................................................. 88114533

(51) Int. Cl.[7] .......................... A61K 31/705; A61K 33/24
(52) U.S. Cl. .............................................. 514/26; 424/649
(58) Field of Search .................................. 514/26; 424/649

(56) References Cited

U.S. PATENT DOCUMENTS 5,958,770 * 9/1999 Cham et al. ............................ 514/26

FOREIGN PATENT DOCUMENTS

0020029 A1 * 10/1980 (EP) ....................................... 514/26

* cited by examiner

*Primary Examiner*—Jerome D. Goldberg
(74) *Attorney, Agent, or Firm*—Fish & Richardson P.C.

(57) ABSTRACT

Disclosed is a pharmacological composition for treating cancer cells, comprising solamargine and a pharmacologically compatible carrier or diluent.

1 Claim, 13 Drawing Sheets

FIG. 12A
FIG. 12B
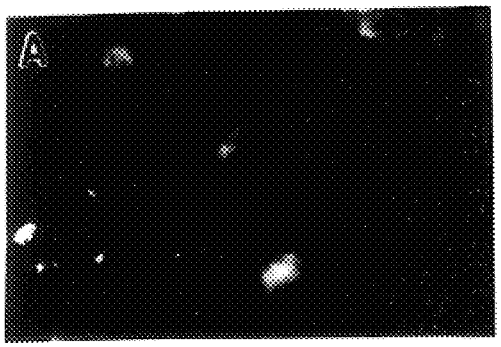
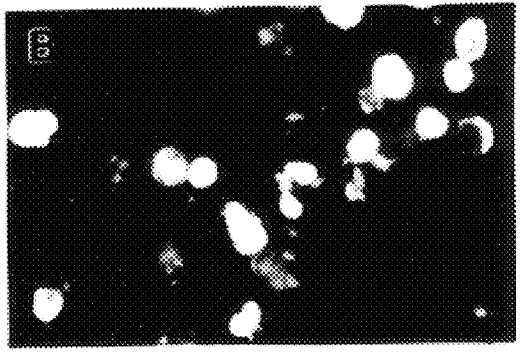
FIG. 12C
FIG. 12D
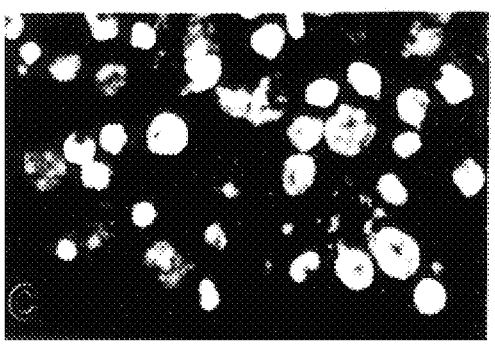
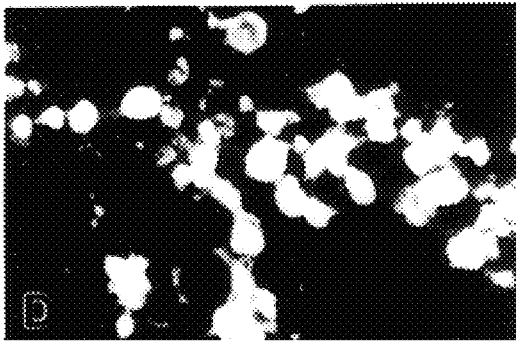

PHARMACOLOGICAL COMPOSITION FOR TREATING CANCER CELLS

BACKGROUND OF THE INVENTION

1. Field of the Invention

The present invention relates to a pharmacological composition for treating cancer cells, and particularly relates to a pharmacological composition consisting of solamargine.

2. Description of the Prior Art

Cancer is the No. 1 cause of death in Taiwan, wherein lung cancer and liver cancer are both major contributors. Official statistical results published in 1999 indicate that the average age of the patients suffering from cancer is gradually decreasing, and that the inhabitants of Taiwan are seriously threaten by various cancers. Scientists around the world are studying the mechanisms of cancer to develop effective drugs for curing or relieving the symptoms of cancers. Currently, many researchers are devoting themselves to finding some effective cancer treating components from herbs.

As mentioned above, liver cancer and lung cancer are the major cancers in Taiwan. The high occurrence of liver cancer in Taiwan relates to the chronic hepatitis caused by hepatitis B virus (HBV); the high occurrence of lung cancer is a worldwide tendency, especially in the Western countries. Lung cancer can be classified into small-cell lung cancer (SCLC) and non-small-cell lung cancer (NSCLC), wherein 25% of lung cancer is SCLC. Because the SCLC cells have smaller size and grow faster than those of the NSCLC, and usually pervasively distributed in the central region of lung, it is difficult to surgically excise SCLC. Unfortunately, SCLC cells pervade to lymphatic tissue and other sites at an early stage, and therefore it is usually the terminal stage when the patient is diagnosed to be suffering from lung cancer.

However, while SCLC is highly sensitive to the present cancer-killing drugs, the drug-resistance of NSCLC cells is hard to overcome in clinical therapy. According to clinical experiences, most of the NSCLC patients can not be effectively controlled by drugs, and the average 5-years survival rate is less than 10%. It is important, therefore, to study and develop effective pharmacological composition to overcome the drug-resistant mechanism of NSCLC.

Due to the ineffectiveness of conventional cancer-killing drugs in improving the condition of cancer patients, scientist has turned to herbs. After screening the cytotoxicity of various components isolated from herbs to cancer cells, the inventors of this present application found that both the lung cancer cells and liver cancer cells are sensitive to solamargine, a steroid glycoalkaloid isolated from Solanum (Alzerreca and Hart, Toxicology Letter, 1982, 12: 151–155). Therefore, a pharmacological composition used to kill cancer cells, and especially lung cancer cells and liver cancer cells, can be developed based on solamargine.

SUMMARY OF THE INVENTION

The object of the present invention discloses a pharmacological composition for treating cancer cells, which consists of solamargine (5~60 $\mu$M), isolated from Solanum, and a pharmacological compatible carrier or diluent, such as alcohol, DMSO, cremophor EL and saline. This pharmacological composition can further comprises a cancer-killing drug, such as cisplatin (20~300 $\mu$M). By combining solamargine with cisplatin, the effective killing of the cisplatin-resistant cancer cells can be enhanced, particularly lung cancer cells.

BRIEF DESCRIPTION OF THE DRAWINGS

The present invention will become more fully understood from the detailed description given hereinbelow and the accompanying drawings, given by way of illustration only and thus not intended to be limitative of the present invention.

FIG. 12 shows TUNEL assay of Hep3B nuclear DNA fragmentation after solamargine treatment (5 $\mu$g/ml) for A, 0 hr; B, 3 hrs; C, 7 hrs; and D, 12 hrs.

DETAILED DESCRIPTION OF THE INVENTION

Figure 1:
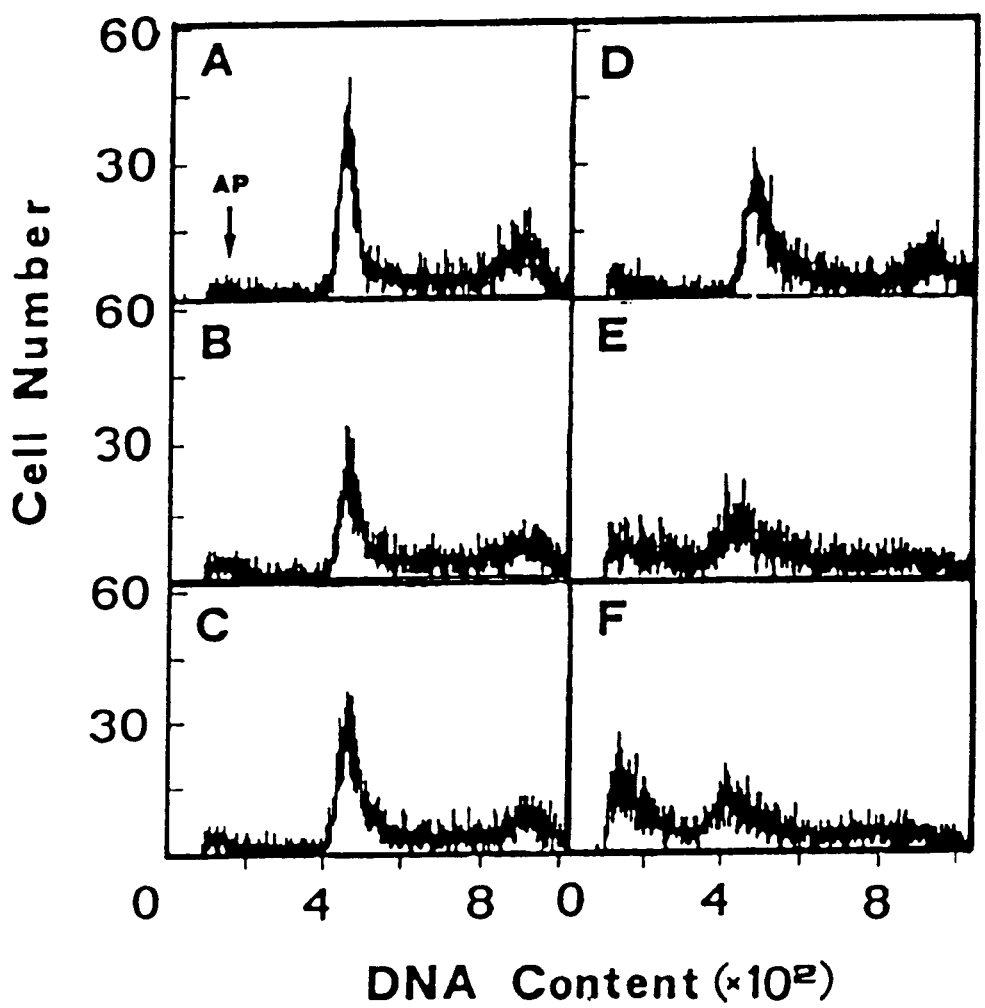
FIG. 1 shows the flow cytometric analysis of the DNA histogram of propidium iodide (PI)-stained Hep3B cells.

Solamargine used hereinafter was extracted from *Solanum incanum* and purified according to the method described hereinblow. The assayed cells included hepatic cells (Hep3B) and lung cancer cells (H441, H520, H661).

In order to observe the morphological change of chromatin of cells after solamargine-treatment, Hep3B cells were treated with solamargine (5 $\mu$g/ml) for 0 hr~12 hrs, then stained with haematoxylin and inspected by light-microscopy (×500). The nuclear DNA fragmentation of solamargine-treated Hep3B cells were determined by TUNEL assay and examined by a fluoro-microscopy; the DNA histogram of propidium iodide (PI)-stained Hep3B cells were analyzed by means of flowcytometry.

The effects of solamargine in various stages of cell cycle were tested by pre-treating the Hep3B cells with cell cycle-blockage agents (e.g. cochicine, cyclosporin A and genistein), thus post-treating with solamargine. The cytotoxicity of Hep3B cells was determined by MTS assay.

It is well known that TNFR-I, TNFR-II, Fas, and caspase-3 and caspase-8 are involved in apoptosis of cells, therefore the gene expression of TNFR-I, TNFR-II, Fas, caspase-3 and caspase-8 in solamargine-treated H441 cells were determined in this example by RT-PCR, followed by Southern-blotting assay.

On the other hand, the TNFR-I and TNFR-II of Hep3B cells induced by solamargine were neutralized with TNFR-I and TNFR-II specific antibodies. Then, the apoptotic properties described above were determined.

Additionally, the inhibition of the proliferation of H441, H520 or H661 cells treated with either solamargine, taxol, cisplatin, or gemcitabine for a period of time was determined.

Also, the synergic effect of solamargine and cisplatin on cisplatin-resistant lung cancer cells (H441, H520, H661) were determined by pre-treating with a constant concentration of solamargine (0, 6, 12, 18 $\mu$M) for 2 hours and post-treating with cisplatin (0, 20, 40, 60, 80 $\mu$M) for 16 hours. Then the synergic cytotoxicity of cells was determined by MTS assay.

EMBODIMENT OF THE INVENTION

Example

Purification of solamargine:

10 kg of *Solanum incanum* was provided and cut into pieces. Then the pieces were transferred to a round-bottom flask and extracted with methanol. Removing the residue, the extract was concentrated by reduced pressure. The obtained concentrated product was dissolved in 3% acetic acid solution, and purified by silica gel column based chromatography using chloroform/methanol (4/1) as the eluent solution to obtain purified solamargine.

The purified solamargine was analyzed by HPLC under the following recipes:

Column: Merck, LiChroCART RP-18 (5 $\mu$m), 4.0×125 mm;
Mobile phase: acetonitrile/$H_2O$=60/40, adjusted to pH 2.5 using phosphoric acid, and filtrated by a 0.45 $\mu$m filter;
Flow rate: 1.0 ml/min.;
UV detector: Spectra-Physics UV2000 at $\lambda$=220 nm;
Internal standard: indomethacin;
Retention time: 5.62 min.
Cell line:

The cell line used in this example included hepatoma cells (Hep3B, obtained from ATCC) and lung cancer cells (H441, H520 and H661, obtained from ATCC).

Preparation of solamargine stock:

The solamargine was dissolved in DMSO to prepare a clear stock solution with a final concentration of 10 mg/ml.

Treatment of cancer cells:

(1) Treating cancer cells with solamargine $10^5$ of either H441 cells, H520 cells or H661 cells were independently suspended in a plate dish containing 0.1 ml of RPMI-1640 medium supplied with 10% fetal calf serum (FCS) and 4 $\mu$g/ml gentamycin (Gibco BRL Co. Ltd, USA), and incubated in a 5% $CO_2$ incubator at 37° C. for 16 hours. Similarly, $10^5$ of Hep3B cells were suspended in a plate containing 0.1 ml of DMEM/F12 medium supplied with 10% FCS and 4 $\mu$g/ml gentamycin (Gibco BRL Co. Ltd, USA), and incubated in a 5% $CO_2$ incubator at 37° C. for 16 hours.

Then, solamargine solutions of different concentration were added to the culture medium to treat the cancer cells. The solamargine stock solution was diluted with the culture medium to desired concentration when used, then a constant volume (2 $\mu$l) of the diluted solamargine solution was add to the culture medium (100 $\mu$l/well), and well-mixed by slightly shaking. Afterwards, the cells were continuously incubated in the incubator for 16 hours. The cytotoxicity of solamargine-treated cancer cells were determined by MTS assay (Cell Titer 96TM AQ (Promega, Madison, USA)).

(2) Treating the cycle-blockage agent pre-treated Hep3B cells with solamargine

Hep3B cells were pre-treated with a cycle-blockage agent, such as cochicine (8 $\mu$g/ml), cyclosporin A (10 $\mu$g/ml) or genistein (20 $\mu$g/ml) for 16 hours to arrest Hep3B cells at different stage of cell cycle. Then, the cycle-blockage agent pre-treated Hep3B cells were post-treated with solmargin (0, 1, 2, 3, 4, 5 $\mu$g/ml) for 16 hours. The cytotoxicity was determined by MTS assay.

(3) Independent treatment of lung cancer cells (H441, H520, H661) with either solamargine, taxol, cisplatin or gemcitabine The lung cancer cells (H441, H520, H661) were independently treated with either solamargine, taxol, cisplatin or gemcitabine for 16 hours according to similar method as described above. The cytotoxicity was determined by MTS assay.

Cytotoxicity assay:

After the treatment was finished, [$^3$H]-thymidine (2 $\mu$Ci) was added to each culture medium, and further co-incubated in a 5% $CO_2$ incubator at 37° C. for 4 hours. Then, PBS containing non-radioactive thymidine (100 $\mu$g/ml) was added to stop the incorporation of [$^3$H]-thymidine. DNA was precipitated by cold 10% TCA solution. The precipitated DNA was washed with 5% TCA, then dried with 95% ethanol. The obtained [$^3$H]-DNA was digested with 0.2M NaOH solution, then transferred to a test tube containing 3 ml of Ecolume scintillation counting solution (ICN Biomedicals). The emitted radioactive particles were counted by a scintillation counter (Packchard Model LS 6800). In addition, the cytotoxicity was determined by MTS assay.

Synergic effect of solamargine and cisplatin on the cisplatin-resistant lung cancer cells (H441, H520, H661):

The lung cancer cells (H441, H520, H661) were incubated according to the method as described above, wherein the cells were pre-treated with solamargine (0, 6, 12, 18 $\mu$M) for 2 hours. Then, the cells were post-treated with cisplatin (dissolved in sterile water) by adding cisplatin solution of different concentrations (0, 20, 40, 60, 80 $\mu$M) to the culture medium and mixing well by slightly shaking. The cells were continuously incubated for 16 hours. The cytotoxicity of solamargine-treated cancer cells were determined by MTS assay. The cytotoxicity was calculated according to the formula: [$O.D._{490\ nm}$ of cisplatin-treated cells/$O.D._{490\ nm}$ of non-treated cells]×100%

Extraction of cellular total RNA

The extraction of cellular total RNA began with collecting the cells and washing with phosphate buffered saline (PBS).

Then, the cells were digested with lysis solution, and extracted with guanidinium thiocyanate. The extract was further centrifuged with 5.7M CsCl/EDTA at 32,000 rpm (Swing-bucket, Beckman L8–70M) for 20 hours to obtain purified total RNA. The content of cellular total RNA is evaluated based on $O.D._{260\ nm}$ of 18 S and 28 S RNA at 260 nm, and the ratio of $O.D._{260\ nm}/O.D._{280\ nm}$.

Preparation of cDNA by reverse-transcription:

cDNA was prepared by using the Advantage™ RT-PCR kit (Clonetech Laboratories., USA), the steps comprising:

(1) 0.2~1 μg of purified total cellular RNA was provided, and DEPC water was added to a final volume of 12.5 μl. 1 μl of Oligo(dT)$_{18}$ primer (20 pmole) was added to form a mixture, then the mixture was heated at 70° C. for 2 minutes to denature the total RNA. Subsequently, the denatured mixture was placed in ice till used.

(2) 4 μl of 5× reaction buffer (50 mM Tris-HCl, 75 mM KCl, 3 mM MgCl$_2$), 1 μl of dNTP mixture (containing 10 mM of each oligonucleotide), 0.5 μl of RNase inhibitor (1 unit/μl), 1 μl of MMLV reverse transcriptase (200 U) were added to the ice-cold denatured mixture in series to a final volume of 20 μl, and well mixed.

(3) After reacting at 42° C. for 1 hour, the temperature was risen to 94° C. and reacted for 5 minutes to remove the activity of the MMLV-RTase and terminate the reaction. The first strand cDNA was obtained after 80 μl of DEPC-water added to a final volume of 100 μl. The obtained cDNA was stored at −70° C.

Polymerase chain reaction (PCR):

10 μl of cDNA was added to an eppendorf, then 10 μl of 10× reaction buffer, 6 μl of 25 mM MgCl$_2$ solution, 1.5 μl of 10 mM dNTP (dilution from 100 mM of each oligonucleotide (dGTP, dATP, dTTP, dCTP)), 2 μl of 50 μM upstream and downstream primers, 0.5 μl of Taq DNA polymerase (5 units/μl) (Promega Corp., Madison, USA) and ddH$_2$O were added to the eppendorf in series to a final volume of 100 μl. The gene expression of β-actin (289 base pairs) and caspase 3 (498 base pairs) before and after treatment with solamargine was detected in this example. The primers used for amplifying β-actin and caspase 3 were lised as following:

β-actin primer pairs:

5'-ACCCACACTGTGCCCATCTA-3' (upstream)

5'-CGGAACCGCTCATTGCC-3' (downstream)

caspase 3 primer pairs:

5'-AGCACTGGAATGACATCTCGGT-3' (upstream)

5'-CAGCATGGCACAAAGCGAC-3' (downstream)

The size of the PCR products of GAPDH, caspase 8, Fas and FADD were 500 bps, 405 bps, 321 bps, and 205 bps, respectively. In addition, these PCR products were amplified by means of commercial MPCR Kits for human apoptosis genes set-4 (Mazim Biotech, CA, USA). The PCR reaction was finished by an autothermal cycler (Perkin Elmer 9600), and the reaction condition of each cycle was: (1) denaturing at 94° C. for 1 minute; (2) annealing at 60° C. for 1 minute; and (3) extension at 72° C. for 1 minute. The reaction involves 35 cycles. After this PCR reaction was finished, 20 μl of the product was separated by ethidium bromide-stained agarose electrophoresis.

Flowcytometry:

The treatment of solamargine was terminated by adding PBS after various treating intervals, then the solamargine-treated cells were washed with PBS and immobilized with 4% paraformaldehyde (in PBS, pH 7.4) at room temperature for 30 minutes. After centrifuging at 1,000 rpm for 10 minutes, 0.1% Triton X-100 (in 0.1% sodium citrate solution) was added to treat for 2 minutes to enhance the penetrability of cells. Then the cells were stained with 10 μg/ml propidium iodide (in PBS) at 37° C. for 30 minutes. Afterwards, the cells were analyzed by detecting the intensity of red fluorescence using a FACScan flowercytometry (Becton Dickinson, San Jose, Calif.). Each sample in this experiment comprises at least 5,000 cells. The obtained data were further analyzed by the LYSIS II software built in the flowcytometry.

Neutralization of TNFR-I and TNFR-II by their specific antibodies $10^5$ Hep3B cells were cultured in a culture medium consisting of 100 μl DMEM/F12 medium (Gibco BRL Co. Ltd., USA) supplied with 10% FCS and 4 μg/ml gentamycin (Gibco BRL Co. Ltd., USA) and incubated in a 5% $CO_2$ incubator at 37° C. for 16 hours. Then, TNFR-I and TNFR-II specific antibodies (10, 50, 100 pg) were respectively added into the independent culture medium to pre-treat the cells for 1 hour to block the function of TNF-receptors. Afterwards, a constant amount of solamargine (6 μM) was added and incubated continuously in a 5% $CO_2$ incubator at 37° C. for 16 hours. The cytotoxicity of solamargine-treated cancer cells were determined by MTS assay. Each data in a test was calculated from duplicated experiments (each experiment consisting of three samples). The cytotoxicity is expressed by: means (%)±S.D.

Results:

FIG. 1 shows the flow cytometric analysis of the DNA histogram of propidium (PI)-stained Hep3B cells. The Hep3B cells were treated with solamargine (5 μg/ml) for A, untreated; B, 30 minutes; C, 1 hour; D, 3 hours; E, 5 hours and F, 7 hours. After treatment, the cells were fixed and coincubated with PI and RNase before recording red fluorescence excited by blue light. A sub-G1 peak, labeled "Ap", appears with the time of incubation. Moreover, the significance of sub-G1 peak of flowcytometry increased with time.

Figure 2:
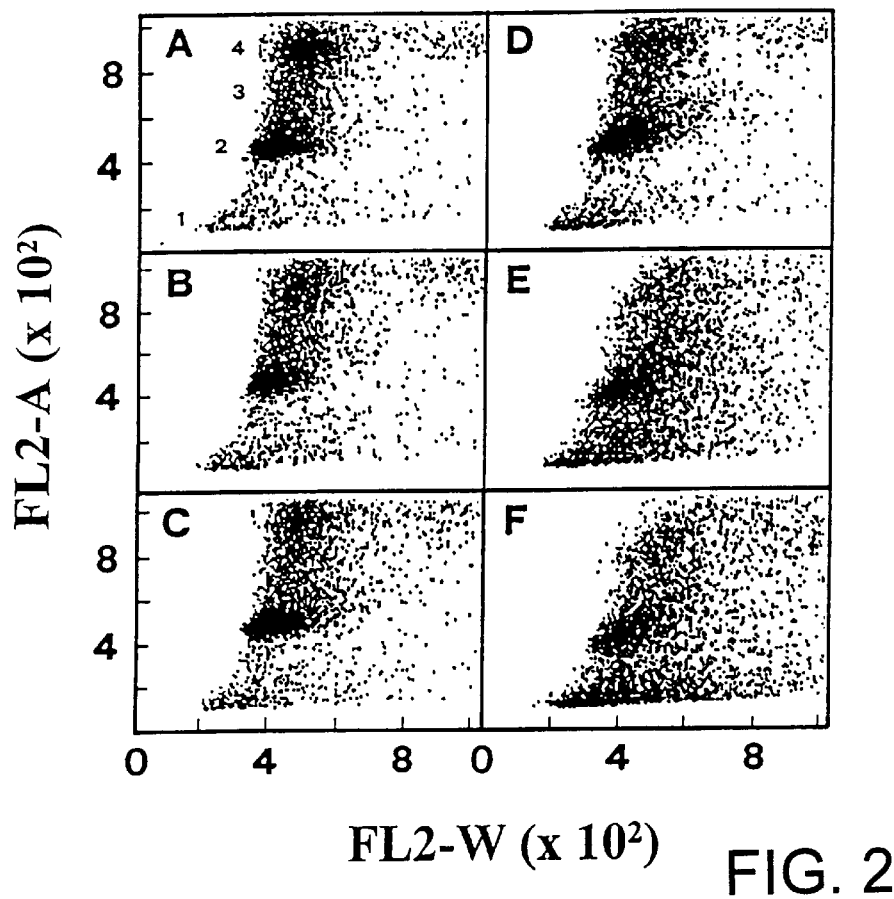
FIG. 2 shows the flow cytometric cytograms of Hep3B cells after treated with solmargine (5 $\mu$g/ml) for A, untreated; B, 30 minutes; C, 1 hour; D, 3 hours; E, 5 hours; and F, 7 hours.

FIG. 2 shows the flow cytometric cytograms of Hep3B cells after treated with solmargine (5 μg/ml) for A, untreated; B, 30 minutes; C, 1 hour; D, 3 hours; E, 5 hours; and F, 7 hours. The cell populations 1, 2, 3 and 4 denote the cell cycle at sub-G1, $G_0/G_1$, S and $G_2/M$ phase, respectively. It is noted that the cell population at G2/M phase (D) is drastically shifted to the sub-$G_1$(E). As shown in FIG. 2, the cells of G2/M stages were shifted to sub-G1 stage, indicating that the solamargine arrested cancer cells at G0/G1 stage and drove cells of G2/M stages to enter apoptosis.

Figure 3:
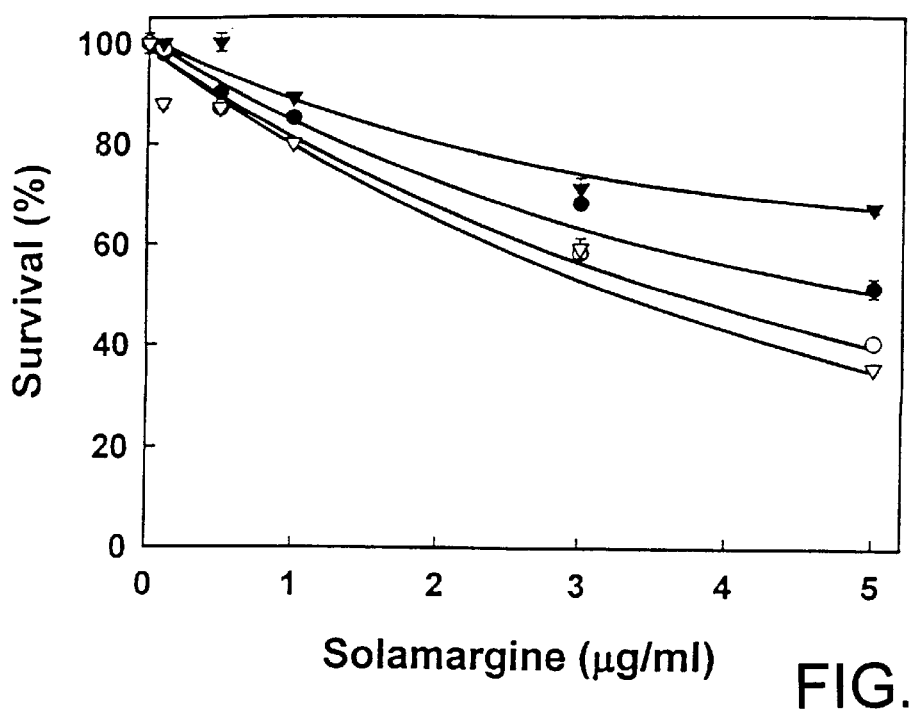
FIG. 3 shows effect of the cycle-blockage agents (●, control; ○, 8 $\mu$g/ml cochicine; ▼, 10 $\mu$g/ml cyclosporin A; ▽, 20 $\mu$g/ml genistein) of human Hep3B cell in solamargine treated cells.

FIG. 3 shows effect of the cycle-blockage agents of human Hep3B cell in solamargine treated cells. Constant amounts of cycle-blockage agents (●, control; ○, 8 μg/ml cochicine; ▼, 10 μg/ml cyclosporin A; ▽, 20 μg/ml genistein) were incubated with increasing concentration of solamargine for 16 hours. The cytotoxicity was determined by MTS assay. As shown in FIG. 3, the results demonstrated that the cells at G2/M stages were sensitive to solamargine.

Figure 5:
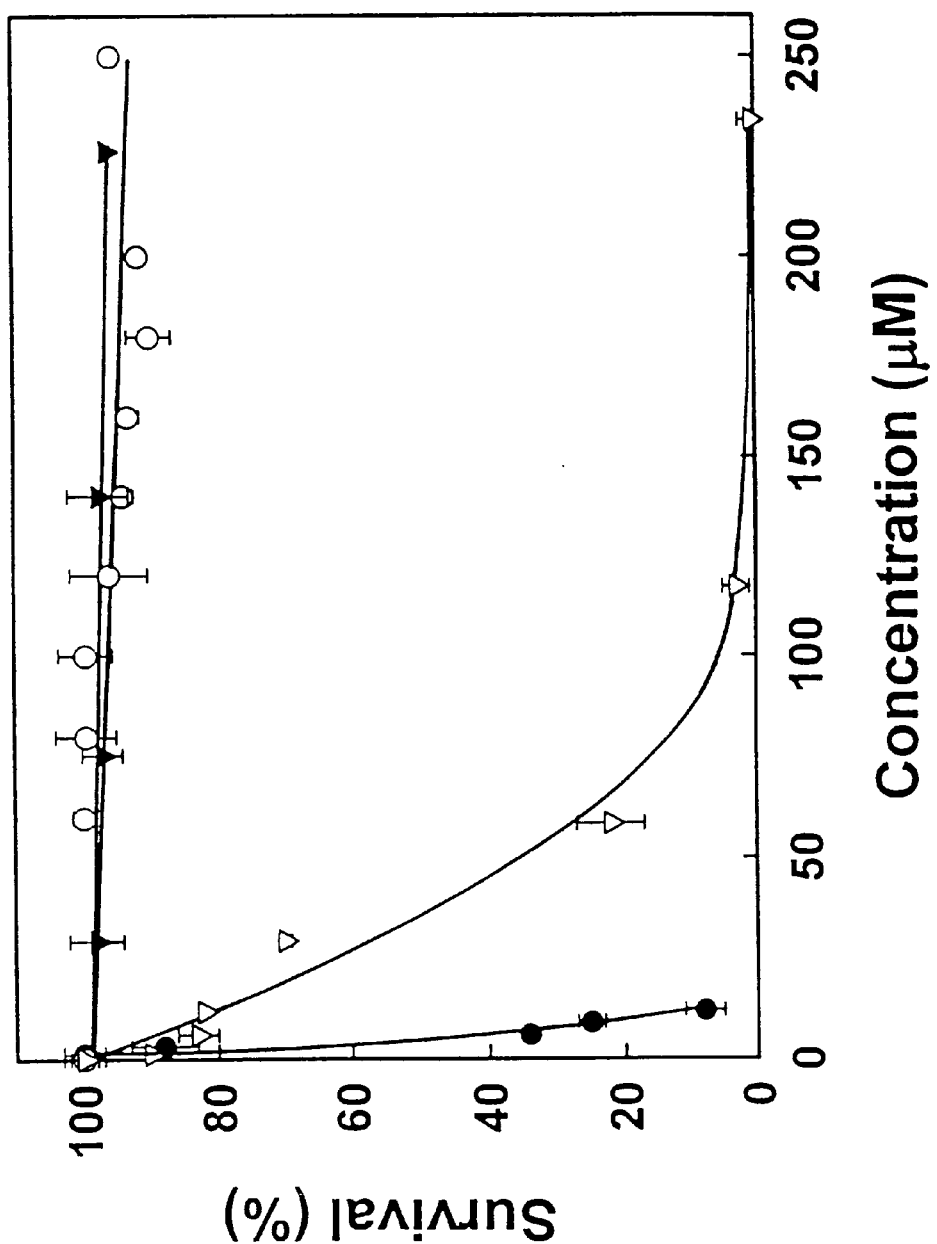
FIG. 5 shows the inhibition of the proliferation of H441 cells treated with either solamargine (●), taxol (▽), cisplatin (▼), or gemcitabine (○) for 16 hours.
Figure 6:
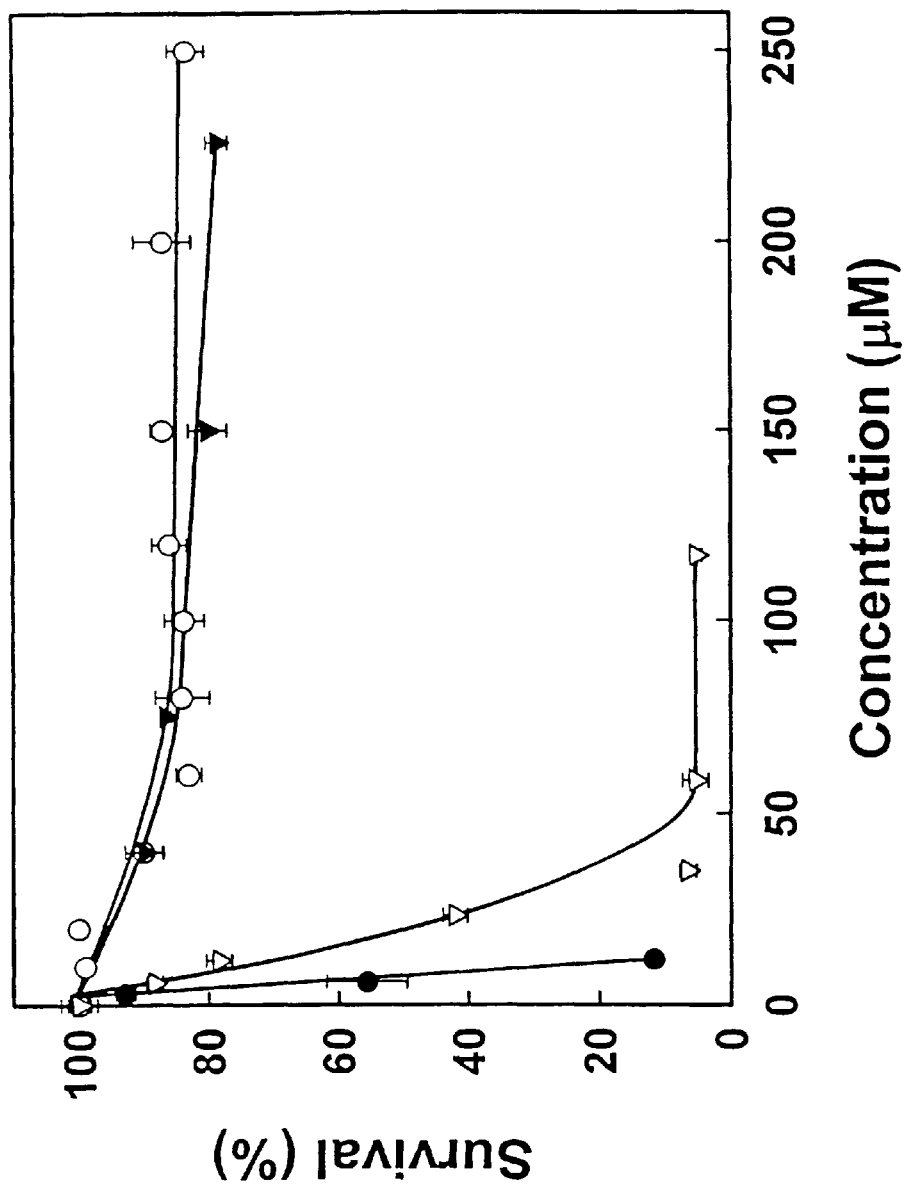
FIG. 6 shows the inhibition of the proliferation of H520 cells treated with either solamargine (●), taxol (▽), cisplatin (▼), or gemcitabine (○) for 16 hours.
Figure 7:
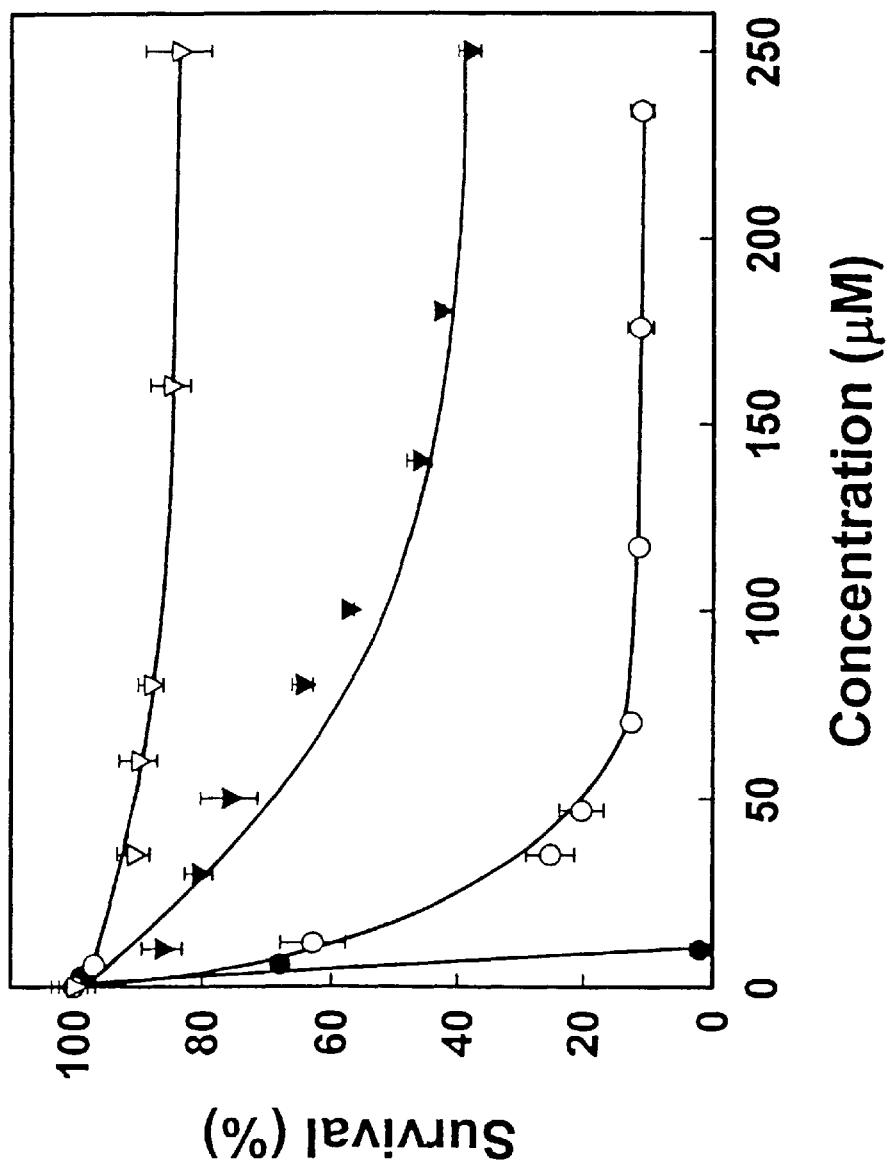
FIG. 7 shows the inhibition of the proliferation of H661 cells treated with either solamargine (●), taxol (○), cisplatin (▼), or gemcitabine (▽) for 16 hours.

Moreover, the cytotoxicity of the solamargine was compared with the conventional drugs, such as taxol, cisplatin and gemcitabine, wherein the lung cancer cells H441, H520 and H661 were used to test. As shown in FIG. 5, the H441 cells were treated with solamargine, taxol, cisplatin and gemcitabine independently for 16 hours. The survival curves indicate that the solamargine according to this present invention has the best cell-killing ability to H441 cells among these treating agents. In addition, solamargine can kill H441 cells to a survival rate less than 10% at a extreme low concentration. The killing effect is more desirable than the clinical cancer-killing drugs, such as taxol, cisplatin and gemcitabine. Similarly, the H520 cells were treated with solamargine, taxol, cisplatin and gemcitabine independently for 16 hours. The survival curves shown in FIG. 6 indicate that the solamargine according to this present invention has the best cell-killing ability to H520 cells among these treating agents. In addition, solamargine can kill H520 cells to a survival rate less than 10% at a extreme low concentration. The killing effect is more desirable than the clinical cancer-killing drugs, such as taxol, cisplatin and gemcitabine. Also, the H661 cells were treated with solamargine, taxol, cisplatin and gemcitabine independently for 16 hours. The survival curves shown in FIG. 7 indicate that the solamargine according to this present invention has the best cell-killing ability to H661 cells among these treating agents. In addition, solamargine can kill H661 cells to a survival rate less than 10% at an extreme low concentration. The killing effect is more desirable than the clinical cancer-killing drugs, such as taxol, cisplatin and gemcitabine.

Figure 8:
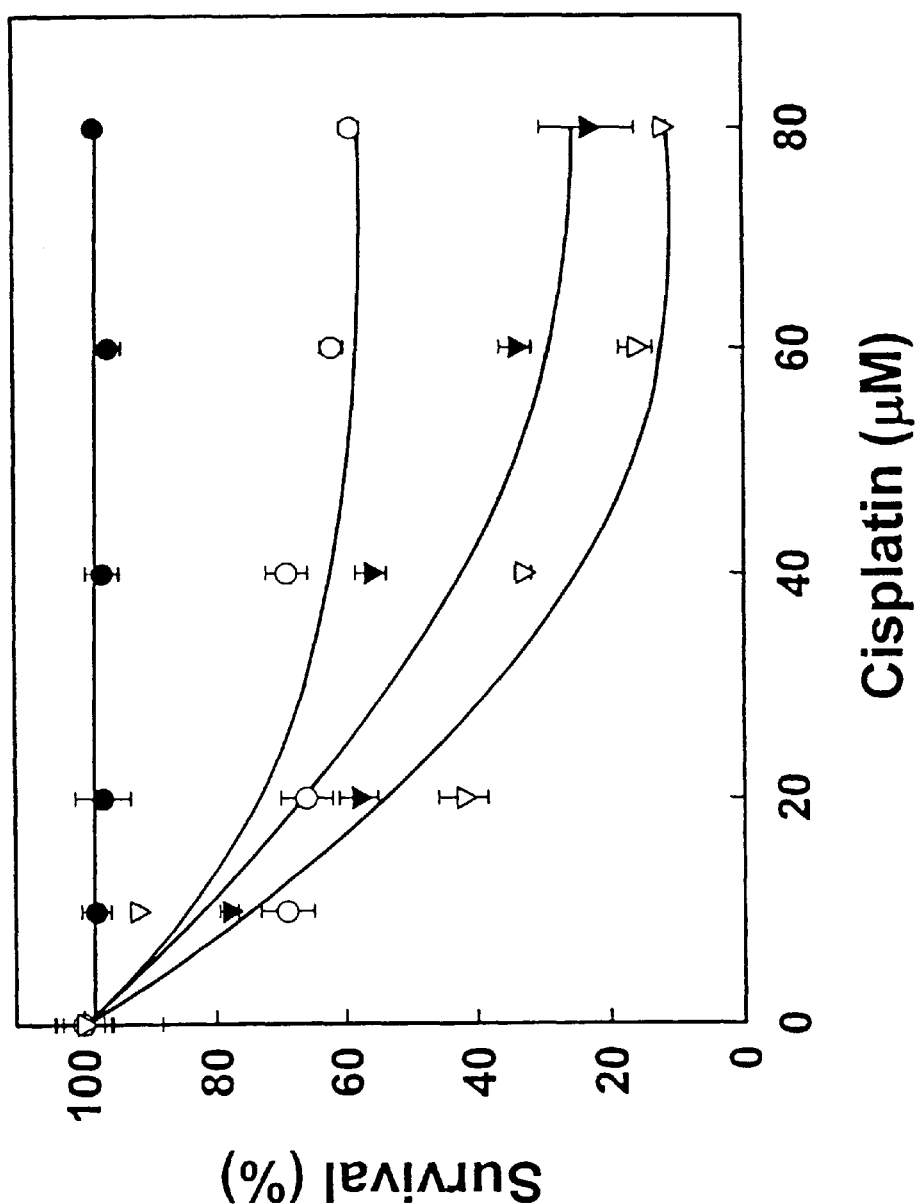
FIG. 8 shows synergic effect of solamargine (●, 0; ○, 6; ▼, 12; ▽, 18 $\mu$M for 2 hours) and cisplatin (0, 20, 40, 60, 80 $\mu$M for 16 hours) on the cisplatin-resistant H441 lung cancer cells.
Figure 9:
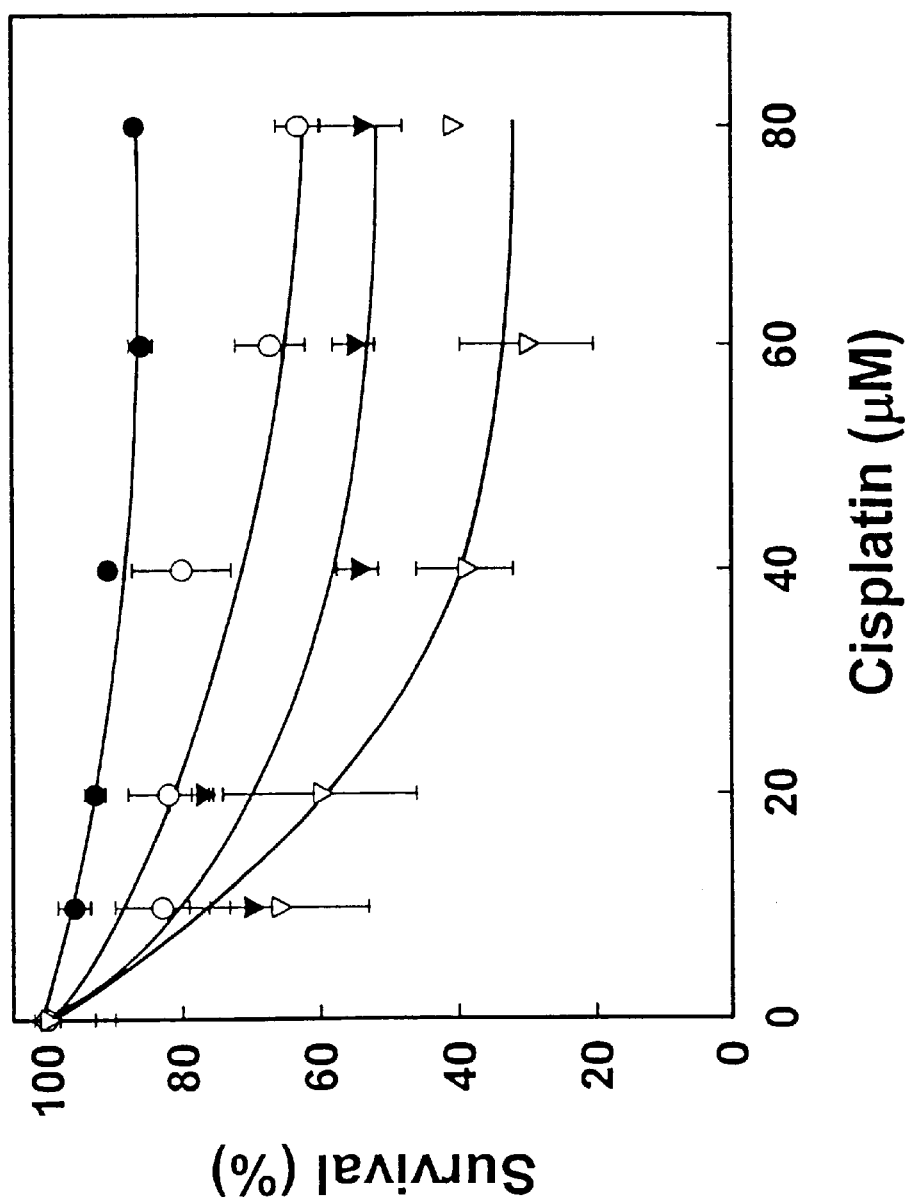
FIG. 9 shows synergic effect of solamargine (●, 0; ○, 6; ▼, 12; ▽, 18 $\mu$M for 2 hours) and cisplatin (0, 20, 40, 60, 80 $\mu$M for 16 hours) on the cisplatin-resistant H520 lung cancer cells.
Figure 10:
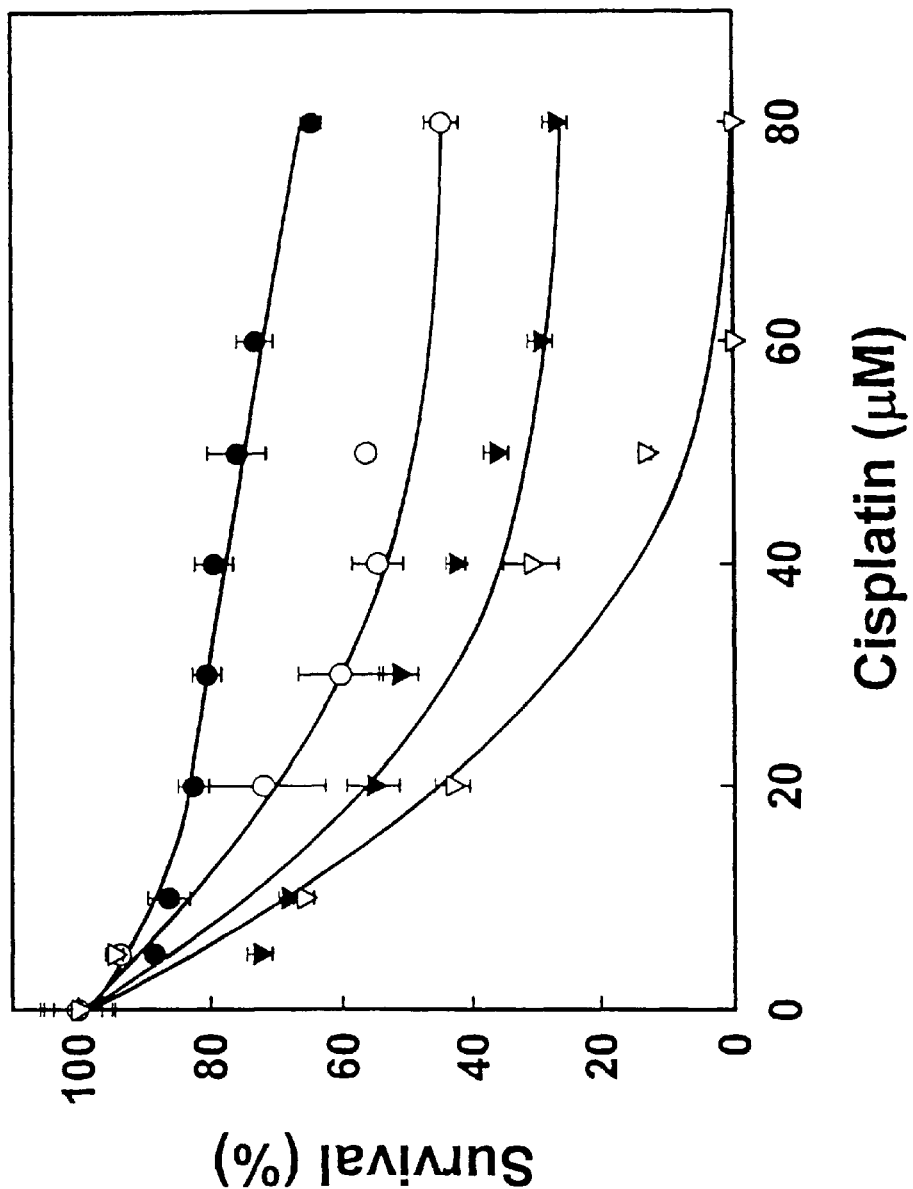
FIG. 10 shows synergic effect of solamargine (●, 0; ○, 6; ▼, 12; ▽, 18 $\mu$M for 2 hours) and cisplatin (0, 20, 40, 60, 80 $\mu$M for 16 hours) on the cisplatin-resistant H661 lung cancer cells.
Figure 11A:
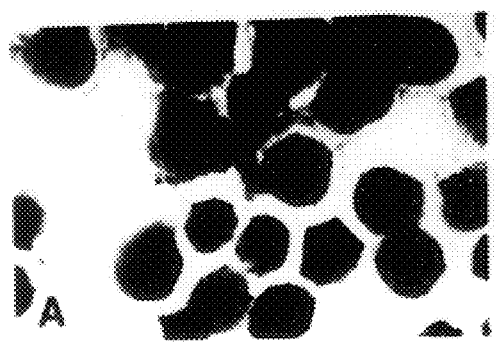
FIG. 11 shows the morphological change of the chromatin of Hep3B after solamargine treatment (5 $\mu$g/ml) for A, 0 hr; B, 3 hrs; C, 7 hrs; and D, 12 hrs.
Figure 11B:
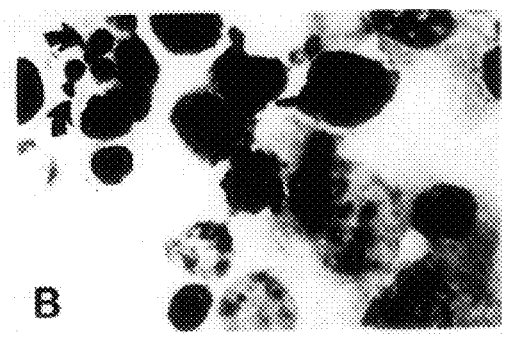
Figure 11C:
Figure 11D:
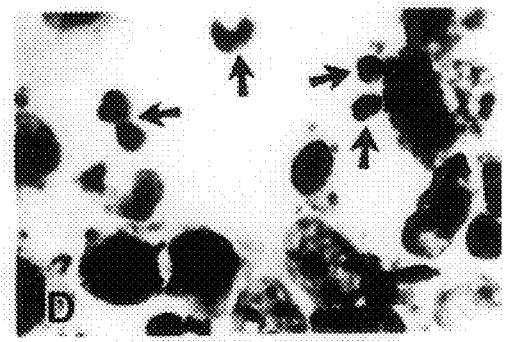

In response to the drug-resistance of NSCLC, the inventors of this invention tried to develop a pharmacological composition consisting of solamargine and another chemical cancer-killing drug to treat the drug-resistant NSCLC. The strategy of this treatment was pre-treating the cancer cells with solamargine for several hours to promote cancer cells to express TNFR, then post-treating with another drugs to kill the cancer cells. In this experiment, the drug-resistant lung cancer cells (H441, H520, H661) were pre-treated with solamargine (●, 0; ○, 6; ▼, 12; ▽, 18 $\mu$M) for 2 hours to enhance the expression of TNFR-I and TNFR-II, then post-treated with cisplatin (0, 20, 40, 60, 80 $\mu$M) for 16 hours. The cytotoxicity of the lung cancer cells were determined by MTS assay as described above. As shown in FIGS. 8, 9 and 10, subtracting the effect caused by solamargine, the cisplatin-resistant H441 cells (FIG. 8), H520 cells (FIG. 9) and H661 (FIG. 10) were sensitive to cisplatin after pre-treating with solamargine. As described above, the synergic lung-cancer killing effect achieved by pre-treating with solamargine and post-treating with cisplatin were more significant than that achieved by single cisplatin-treatment.

In order to study the effect of lethal mechanism of the hepatic cancer cells (Hep3B) and lung cancer cells (H441, H520 and H661 cells) caused by the solamargine, this example used the method described above to test the change of the morphology of the cancer cells and the composition of DNA therein. The apoptosis can regulate the growth of cells, and play an important role in physiological death of cells, therefore it becomes an important subject for developing cancer-killing drugs. During apoptosis, the fragments of dead cells will rapidly be absorbed through phagocytosis by the cells surrounded thereof and macrophages, therefore no inflammation occurs. Recently, apoptosis has become an studying subject in Oncology. Apoptosis is characterized by apoptotic bodies, nuclear condensation and DNA fragmentation. The apoptotic cells and necrotic cells can be divided by a flowcytometry, wherein the sub-G1 peak in DNA histogram is regarded as a typical mark of cellular apoptosis. In accordance, the apoptotic characterizations including chromatin condensation and DNA fragmentation were observed by fluorescent clouration and TUNEL assay.

FIG. 11 shows the morphological change of the chromatin of Hep3B after solamargine treatment. Hep3B cells were treated with solamargine (5 $\mu$g/ml) for A, 0 hr; B, 3 hrs; C, 7 hrs; and D, 12 hrs. The cells were stained with haematoxylin and inspected by light-microscopy (×500). The apoptotic cells reveal cell shrinkage, condensation of chromatin and nuclear fragmentation as indicated by arrows. As shown in FIG. 11, the shrinkage of cells, chromatin condensation and nuclear fragmentation were increased with the increasing treating time (as indicated by arrows in FIGS. 11C and 11D).

Similarly, the changes of the nucleus of the cancer cell before and after solamargine-treatment (5 $\mu$g/ml) (A, 0 hr; B, 3 hrs; C, 7 hrs; and D, 12 hrs) were determined by TUNEL assay. As shown in FIG. 12, the results indicate that the significance of nuclear fragmentation increased with increasing treating time.

Figure 13:
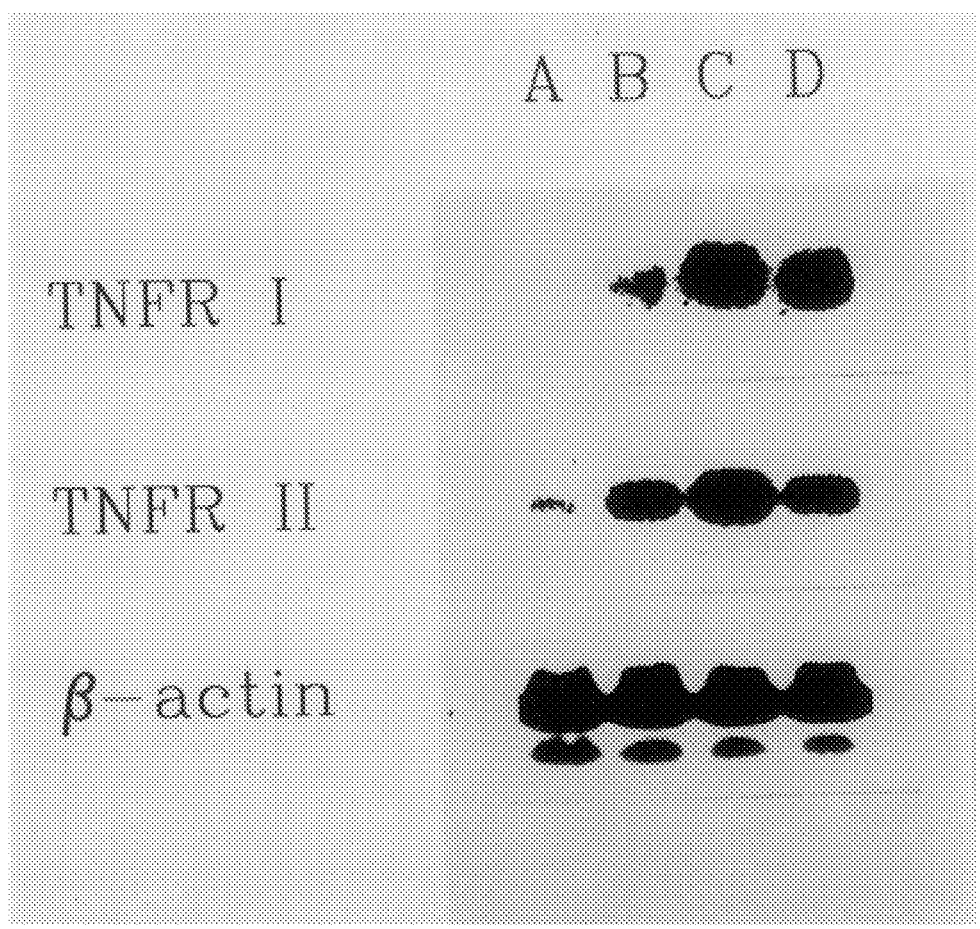
FIG. 13 shows the gene expression of TNFR I and II in Hep3B cells treated with solamargine (5 $\mu$g/ml) for A, 0 minutes; B, 15 minutes; C, 30 minutes; and D, 60 minutes.

FIG. 13 shows the gene expression of TNFR-I and TNFR-II in Hep3B cells treated with solamargine (5 $\mu$g/ml) for A, 0 minutes; B, 15 minutes; C, 30 minutes; and D, 60 minutes. The $\beta$-actin was as a internal control. Normalized by the internal control ($\beta$-actin), the results indicate that both the expression of TNFR-I and TNFR-II increase with the interval of solamargine-treatment.

Figure 4:
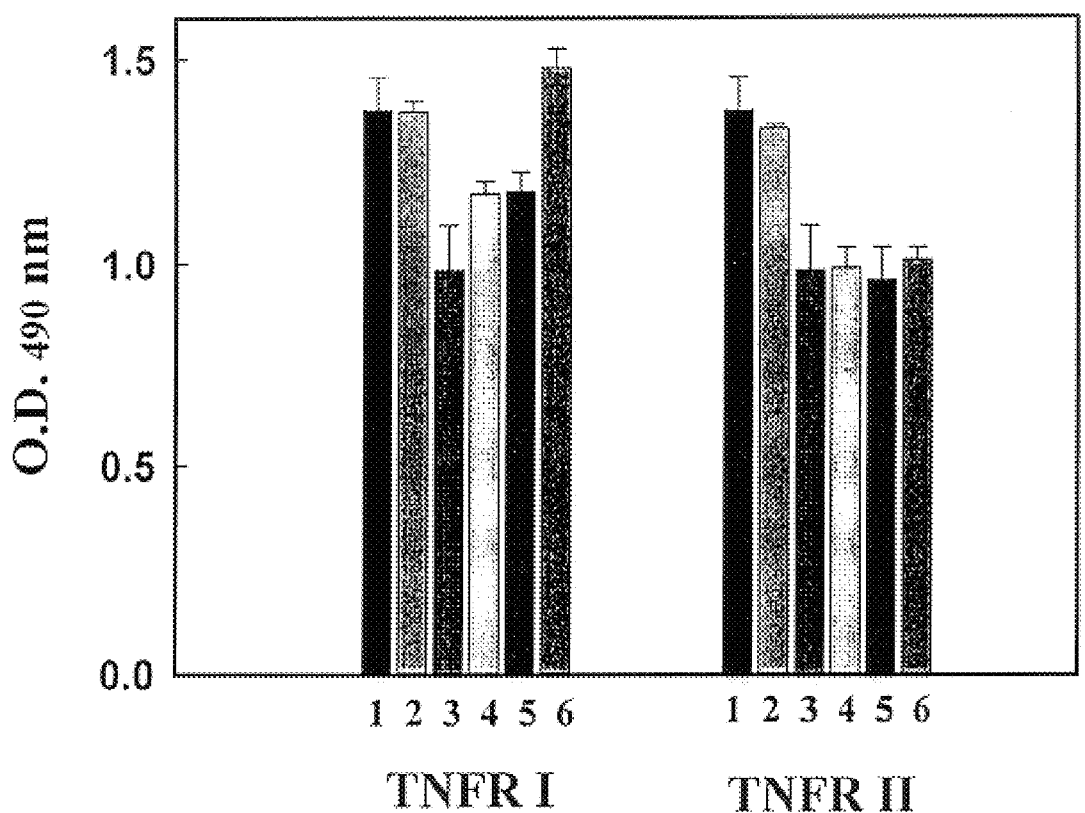
FIG. 4 shows neutralization of the solamargine-induced apoptosis of human Hep3B cells by TNFR-I and TNFR-II specific antibodies.

On the other hand, the TNFR-I and TNFR-II induced by the solamargine were neutralized by adding the TNFR-I and TNFR-II specific antibodies. As shown in FIG. 4, Bar 1 denotes control; Bar 2 denotes treatment with Ab (100 pg); Bar 3 denotes treatment with solamargine (5 $\mu$g/ml) for 16 hours; Bar 4 denotes pre-treatment with Ab (10 pg) for 2 hours, and post-treatment with solamargine (5 $\mu$g/ml) for 16 hours; Bar 5 denotes pre-treatment with Ab (50 pg) for 2 hours, and post-treatment with solamargine (5 $\mu$g/ml) for 16 hours; Bar 6 denotes pre-treatment with Ab (100 pg) for 2 hours, and post-treatment with solamargine (5 $\mu$g/ml) for 16 hours. Accordingly, the cytotoxicity of solamargine can be neutralized by the specific antibodies of TNFR-I, but the specific antibodies of TNFR-II lacks this blocking ability. The obtained results indicate that TNFR-I plays a key role in the apoptosis mechanism leading to the death of cancer cells caused by solamargine.

Figure 14:
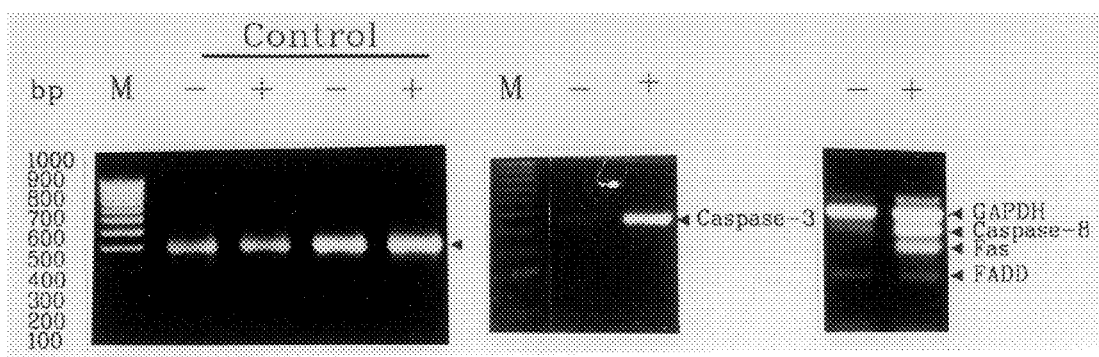
FIG. 14 shows activation of Fas, caspase-3, and caspase-8 of H441 cells after treated with solamargine (12 $\mu$M) for 1 hour.

FIG. 14 shows activation of Fas, caspase-3, and caspase-8 of H441 cells treated with solamargine (12 $\mu$M) for 1 hour. After treatment, the total RNA of H441 cells was extracted for RT-PCR using $\beta$-actin as a control. Symbol "+" and "−" denote solamargine treated and untreated H441 RNA, respectively. The primer sequences of $\beta$-actin and caspase-3 were indicated in "Materials and Methods". The RT-PCR for Fas and caspase-8 were determined by MPCR kit for human apoptosis genes set-4 (Maxim Biotech, San Francisco, USA). The house-keeping gene GAPDH was amplified as an internal control. In addition to enhancing the expression of TNFR-I and the TNFR-II (FIG. 13), Fas was also enhanced (FIG. 14). The death of cancer cells were caused by the apoptotic hydrolytic enzyme (caspase-8 and caspase-3) (FIG. 14) activated by the signals generated by FADD (Fas-associated Death Domain) (FIG. 14).

Both in vivo and in vitro experiment indicate that TNF$\alpha$ is capable to kill cancer cells. The over-expressed receptors of TNF$\alpha$, TNFR-I and TNFR-II, will lead to apoptosis of cancer cells. On the other hand, TNFR-I can cause apoptosis of hepatoma cells by itself; however, the apoptosis of PC60 cells (Rat/mouse T cells hybridoma) only occurs when both TNFR-I and TNFR-II express simultaneously. TNFR-I plays a role in transducting the signals of TNF to various cells, but TNFR-II was only effective to lymophocytes, and involved in inducing growth, differentiation and hormone-generation of cells. The over-expression of TNFR-I and TNFR-II will result in cellular apoptosis. The data indicates that the solmargine can enhance the expression of the TNFR-I, therefore the apoptosis of hepatic cancer cells can be promoted by the enhanced TNFR-I.

Moreover, the observed results, such as nuclear condensation, DNA fragmentation and Sub-G1 peak, demonstrate that solamargine promotes the apoptosis of cancer cells. It is found that the apoptosis of cancer cells caused by solamargine is achieved by activating the TNFRs and Fas of cancer cells to activate apopotic relating cellular hydrolytic enzyme (e.g. caspase-8 and caspase-3). Therefore, the solamargine extracted from *Solanum incanum* can be used to kill cancer cells by promoting the apoptosis of human hepatic cancer cells and lung cancer cells.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A synergistic pharmaceutical composition for treating lung cancer cells or liver cancer cells, the composition comprising solamargine in the range of 5 to 60 $\mu$M; cisplatin in the range of 20 to 300 $\mu$M; and a pharmacologically compatible carrier or diluent selected from the group consisting of alcohol, DMSO, cremophor EL, and saline.

* * * * *